(12) United States Patent

Tansley et al.

(10) Patent No.: US 8,900,114 B2
(45) Date of Patent: Dec. 2, 2014

(54) PULSATILE BLOOD PUMP

(75) Inventors: Geoffrey Douglas Tansley, Kegworth (GB); David Richens, Nottingham (GB)

(73) Assignee: Nottingham University Hospitals NHS Trust, Nottingham (GB)

( * ) Notice: Subject to any disclaimer, the term of this patent is extended or adjusted under 35 U.S.C. 154(b) by 490 days.

(21) Appl. No.: 12/679,651

(22) PCT Filed: Sep. 29, 2008

(86) PCT No.: PCT/GB2008/003309
§ 371 (c)(1),
(2), (4) Date: Mar. 23, 2010

(87) PCT Pub. No.: WO2009/040560
PCT Pub. Date: Apr. 2, 2009

(65) Prior Publication Data
US 2010/0204539 A1 Aug. 12, 2010

(30) Foreign Application Priority Data
Sep. 28, 2007 (GB) .................................. 0718943.4

(51) Int. Cl.
*A61N 1/362* (2006.01)
*A61M 1/12* (2006.01)
*A61M 1/10* (2006.01)
(52) U.S. Cl.
CPC ............... *A61M 1/1037* (2013.01); *A61M 1/12* (2013.01); *A61M 1/1086* (2013.01); *A61M 1/127* (2013.01)
USPC .......................................................... 600/16
(58) Field of Classification Search
USPC .................................................... 600/16–18
See application file for complete search history.

(56) References Cited

U.S. PATENT DOCUMENTS 3,550,162 A 12/1970 Huffman et al.
4,015,590 A 4/1977 Normann
(Continued)

FOREIGN PATENT DOCUMENTS

EP 1318848 B1 7/2008
FR 2 766 373 A1 1/1999
(Continued)

OTHER PUBLICATIONS

International Search Report dated Jan. 21, 2009 for International Application PCT/GB2008/003309, 5 sheets.

*Primary Examiner* — Scott Getzow
(74) *Attorney, Agent, or Firm* — LeClairRyan, a Professional Corporation

(57) ABSTRACT

There is provided a pulsatile blood pump (10) for implantation into a patient. The pulsatile blood pump comprises a substantially tubular body (12) a flexible membrane (14) and a port (16). The substantially tubular body is for replacing a resected portion of a blood vessel of the patient. The substantially tubular body has first and second ends with a blood passageway extending therebetween for the passage of blood. The flexible membrane is attached to the tubular body so as to form a fluid chamber between the flexible membrane and an inner surface of the tubular body. The flexible membrane thereby separates the fluid chamber from the blood passageway. The tubular body comprises the port. The port is arranged to allow fluid to flow into and out of the fluid chamber such that the volume of the fluid chamber increases and the volume of the blood passageway decreases when fluid flows into the fluid chamber via the port, and such that the volume of the fluid chamber decreases and the volume of the blood passageway increases when fluid flows out of the fluid chamber via the port. The blood pump is thereby enabled to pump blood along the blood passageway.

24 Claims, 9 Drawing Sheets

(56) References Cited

U.S. PATENT DOCUMENTS

| | | |
|---|---|---|
| 4,195,623 A | 4/1980 | Zeff et al. |
| 4,250,872 A | 2/1981 | Tamari |
| 4,697,574 A * | 10/1987 | Karcher et al. ............ 600/17 |
| 4,733,652 A | 3/1988 | Kantrowitz et al. |
| 5,145,333 A * | 9/1992 | Smith ............ 417/405 |
| 6,030,335 A | 2/2000 | Franchi |
| 6,050,932 A | 4/2000 | Franchi |
| 6,210,318 B1 | 4/2001 | Lederman |
| 6,468,200 B1 | 10/2002 | Fischi |
| 7,347,811 B2 * | 3/2008 | Peters et al. ............ 600/18 |
| 2003/0032854 A1 * | 2/2003 | Palmer ............ 600/16 |

FOREIGN PATENT DOCUMENTS

| | | |
|---|---|---|
| WO | WO00/35515 | 6/2000 |
| WO | WO2004/045677 A1 | 6/2004 |

* cited by examiner

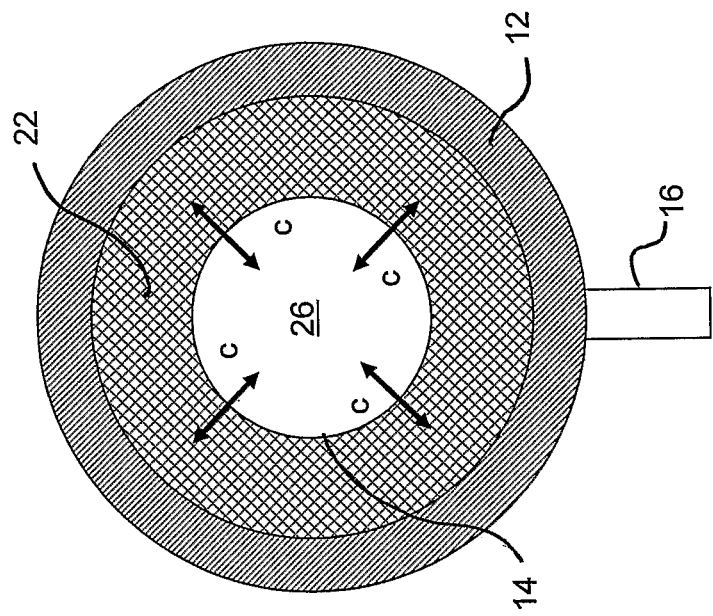
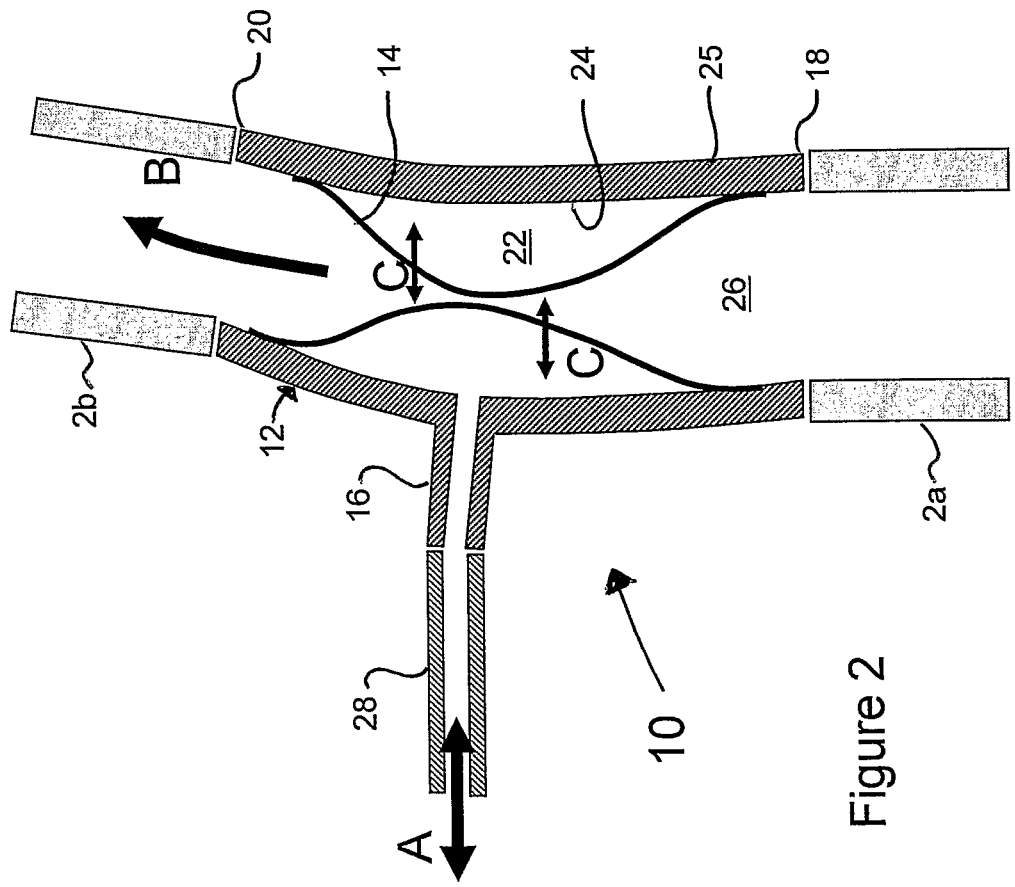

Figure 7
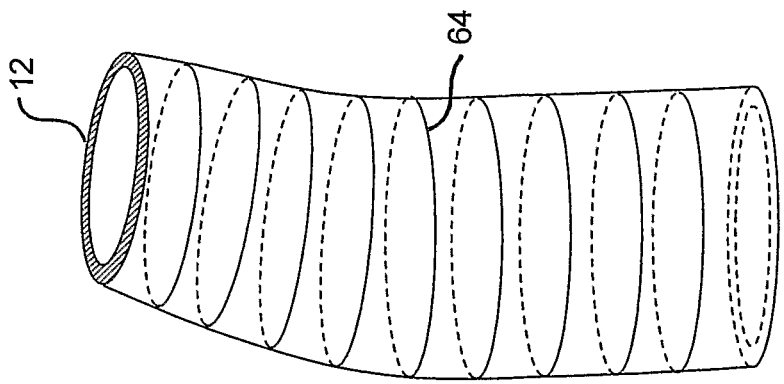
Figure 7c
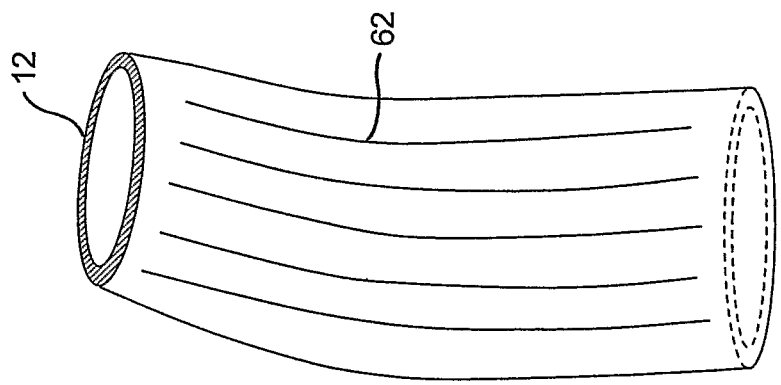
Figure 7b
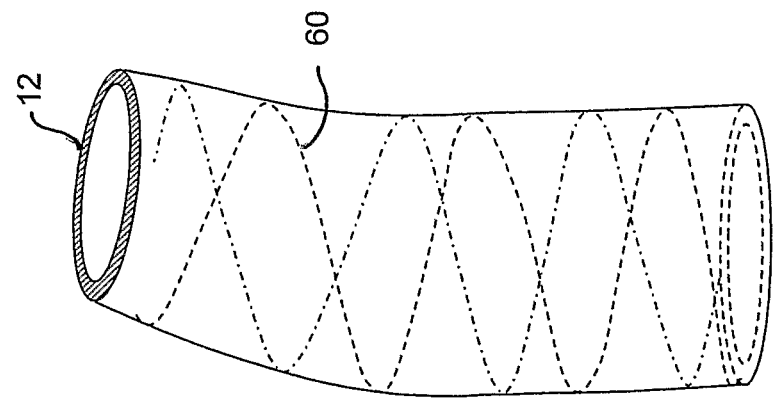
Figure 7a

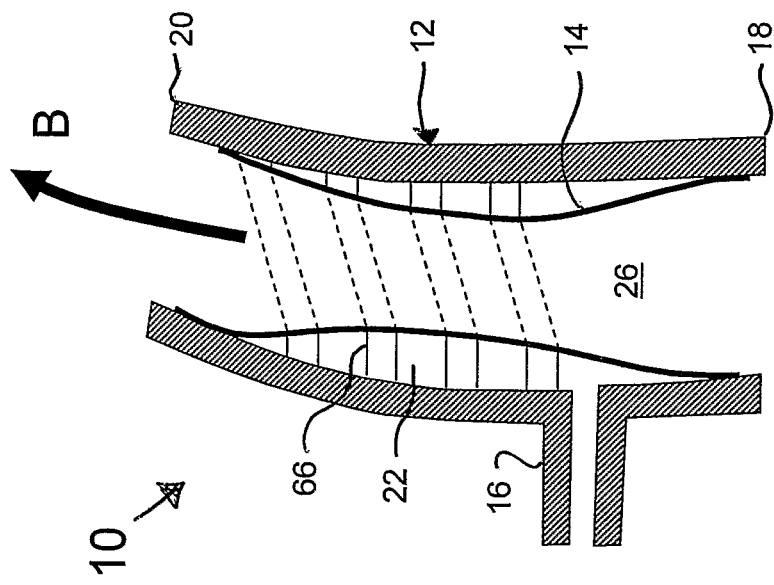
Figure 8b
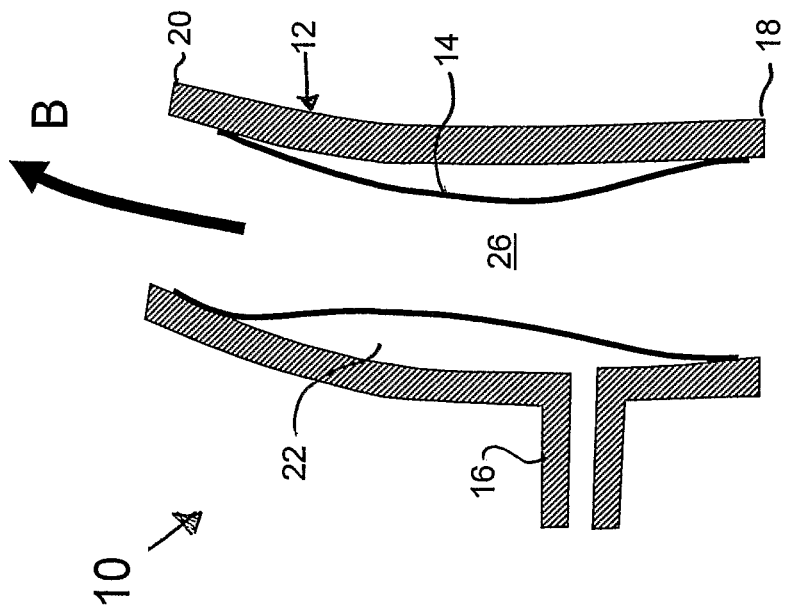
Figure 8a
Figure 8

PULSATILE BLOOD PUMP

CROSS-REFERENCED TO RELATED APPLICATION(S)

This application is a National Phase Patent Application of International Application Number PCT/GB2008/003309, filed on Sep. 29, 2008, which claims priority to and the benefit of GB Application No. 0718943.4, filed Sep. 28, 2007.

FIELD OF THE INVENTION

The present invention relates to a pulsatile blood pump for implantation into a patient. The invention also relates to a blood pump system incorporating such a pulsatile blood pump, and to a method for the treatment of heart failure in a patient.

BACKGROUND OF THE INVENTION

Heart failure is a major cause of death in the developed and developing world; it is estimated that there are currently 901,500 sufferers in the United Kingdom with 65,000 new cases added annually. The British Heart Foundation estimates the annual cost of heart failure is £625 million in the UK alone. In the United States, the corresponding statistics are 5,000,000 sufferers with 550,000 new cases annually and an annual cost to the US economy of $296,000 million. The World Health Organisation estimates that Cardiovascular Disease, around 7% of which is heart failure, contributed to ⅓ of all deaths worldwide and will be the major cause of death by 2010.

The prognosis for heart failure sufferers is poor, with just less than 40% dying within the first year. Furthermore, 5% of all deaths in the UK, approximately 24,000 per annum, are attributable to heart failure. Around 40% of these patients suffer from impaired left ventricular systolic function and could benefit from mechanical support e.g. with a Left Ventricular Assist Device (LVAD). The best therapy for many of these patients would be heart transplantation; however the demand for donor hearts in the USA alone is around 100,000 per annum and far exceeds the 2,200 donor hearts available per annum. The other main therapies commonly available are medical, such as inotropes, ACE inhibitors, Beta blockers, diuretics and nitrates, or are mechanical support therapies, such as the use of a Total Artificial Hearts (TAHs) or Ventricular Assist Devices.

There is a continuum of treatment modalities for patients suffering chronic heart failure. As the disease progresses patients will receive increasingly aggressive medical therapies, but most patients become refractory to medical therapies at some point and their health will decline. Patients eligible for cardiac transplantation would typically receive medical therapies whilst awaiting transplantation; if their condition deteriorated then mechanical "bridge to transplantation", may be adopted in the form of a mechanical support device such as an Intra-Aortic Balloon Pump (IABP), Extra-Aortic Balloon Pump (EABP), or other LVAD. Patients who are supported in bridge to transplantation whilst awaiting transplantation are in a better state of health at the time of transplantation, are more likely to survive transplant surgery and have a better long-term prognosis. Patients ineligible for transplantation typically follow a medical therapy-only path, though with the most aggressive health-care providers may receive mechanical support, e.g. a LVAD or a TAH in "destination therapy".

Several mechanical devices are currently available or are in development which support cardiac function in heart failure. Rotary Blood Pumps (RBPs) take blood typically from the ventricle of the native heart, energise it through the action of a rotating impeller, and deliver the blood to the ascending aorta. These devices allow the patient to ambulate, but do not produce pulsatile blood flow as does the native heart. In contrast, RBPs typically act at a constant rotational speed, can be difficult to control, and are expensive in their implanted form. IABPs, such as those described in U.S. Pat. No. 6,210,318 and EP0192574, are well established technology and comprise small balloons which are inserted into the aorta and which are inflated and deflated, typically in anti-phase with the native heart, through the action of pneumatic fluid acting behind a flexible polymeric membrane. IABPs cannot be deployed for long periods of time since their thin silicone membranes are prone to rupture and their cannulae can cause thromboembolism. EABPs, such as those described in EP1318848, EP1560614, and U.S. Pat. No. 4,733,652, address some of the problems with IABPs through being attached to the external surface of the aorta rather than being implanted within the aorta. Disadvantages of EABPs can include atheromous emboli through interaction with the aortic wall, and migration and interference with neighbouring structures, e.g. erosion of the pulmonary artery or lungs. Other technologies which similarly augment blood flow using balloon pumps include: a balloon pump for insertion into the descending aorta described in U.S. Pat. No. 6,030,355, but this device has a rigid outer body which precludes its implantation at the optimal position in the lower ascending aorta where pumping effect is optimised; and the conduit mounted balloon pumps described in U.S. Pat. Nos. 4,195,623 and 4,015,590 which similarly are non-optimally positioned.

The present invention seeks to provide an alternative pump which provides various advantages over those of the prior art when used in cardiac support.

SUMMARY OF THE INVENTION

According to a first aspect of the present invention, there is provided a pulsatile blood pump for implantation into a patient. In this context, the term "pulsatile blood pump" means a pulsatile pump suitable for pumping blood. Although the pulsatile blood pump of the first aspect of the present invention is suitable for pumping blood, it could also be used to pump other fluids if desired. The pulsatile blood pump comprises a substantially tubular body, a flexible membrane and a port. The substantially tubular body is for replacing a resected portion of a blood vessel of the patient. The substantially tubular body has first and second ends with a blood passageway extending therebetween for the passage of blood. The "substantially" wording means that the cross section of the tubular body need not be exactly circular. For example, an oval cross-section might be considered to be "substantially" circular. In addition, the cross section of the substantially tubular member may change in shape and/or size axially along its length so as to best match the portion of blood vessel that has been removed or so as to afford other benefits whilst in use. The flexible membrane is attached to the tubular body so as to form a fluid chamber between the flexible membrane and an inner surface of the tubular body. The flexible membrane thereby separates the fluid chamber from the blood passageway. The tubular body comprises the port. The port is arranged to allow fluid to flow into and out of the fluid chamber such that the volume of the fluid chamber increases and the volume of the blood passageway decreases when fluid flows into the fluid chamber via the port, and such that the volume of the fluid chamber decreases and the volume of the blood passageway increases when fluid flows out of the fluid chamber via the port. The blood pump is thereby enabled to pump blood along the blood passageway.

Thus, the outflow from the native heart may be augmented through the use of the blood pump of the present invention. The blood pump is surgically placed interpositionally within the aorta (i.e. the blood pump is implanted into the aorta by end-to-end anastomosis to replace a resected portion of the aorta). The cross-sectional area of the blood passageway through the blood pump is caused to contract due to the flow of fluid into and out of the fluid chamber between the tubular body and the flexible membrane of the blood pump. The blood pump may be used in the temporary or long-term treatment of patients suffering heart failure through intermittent or temporary continuous use when counter-pulsed with the natural heart. Additional embodiments can also be contemplated so as to reduce the workload required from the native heart, to augment coronary artery perfusion, and/or to treat other circulatory diseases by introducing such a blood pump into the peripheral circulation.

Patients who would most benefit from use of the blood pump of the present invention may be divided into groups, as described below.

The first group of patients who would derive a significant benefit are patients needing temporary support or bridge to recovery treatment. This group of patients is refractory to medical therapies and will present with declining cardiac and end-organ function, but when supported with a mechanical device will recover cardiac function, typically within around twenty weeks of mechanical support, such that support may then be withdrawn. However, current mechanical LVADs do not incorporate one-way valves making it infeasible to leave them in-situ and deactivated due to significant retrograde flow through them once they have been inactivated. Current LVADs therefore do not provide a life-line to recovered patients, and re-operation is necessary to implant an additional device if cardiac function declines once again. In contrast, the present invention will allow support to be withdrawn on recovery, but for the blood pump to remain in place should intermittent support be required thereafter.

The second group of patients for whom the present invention would be particularly beneficial are patients needing long term chronic support. This group of patients will never recover cardiac function and will be maintained on medical therapies in the long term. The "healthier" of these are minimally supported with medical therapies but require more aggressive support intermittently; typically such patients would be admitted to hospital for one or two weeks respite and receive low doses of inotropes and diuretics which is sufficient to reduce ventricular overload, to restore end organ function and to promote a feeling of well being. Patients receiving more aggressive medical therapies need additional support in times of crisis and would be admitted to intensive care and aided with an IABP such as those of U.S. Pat. No. 6,210,318 and EP0192574. Patients with the worst prognosis may well find themselves on the heart transplant list. A small number of these patients will suffer failing health whilst on the transplant list and will need mechanical assist to bridge them to transplantation. The present invention promises to be a useful treatment modality in each of these scenarios. For the "healthier" patients, treatment may be augmented with the blood pump of the present invention, in addition to medical therapy to provide respite. Once installed, and for subsequent readmission, use of the present blood pump can be very quickly effected and will be fast acting. For patients on higher doses of medication in crisis, the present invention will allow speedier deployment and will allow the patient to be ambulatory and reduce the risk of infection posed by IABPs, as described further below. The present invention will greatly reduce the cost of bridge-to-transplantation by removing the need for an implanted VAD or the need for intensive care beds that would have been required if an external VAD were used.

In one embodiment of the present invention, the flexible membrane is formed as a sheet and is attached across a chord of the tubular body such that the fluid chamber and the blood passageway are disposed side by side within the tubular body. In an alternative embodiment, the flexible membrane is formed as a tube and is attached at or near each end of the tubular body such that the blood passageway is disposed concentrically within the fluid chamber.

As noted above, the flexible membrane is attached to the tubular body. Optionally, the flexible membrane is attached to the inner surface of the tubular body. It may be attached in a parallel or doubled-back configuration. Alternatively/additionally, the flexible membrane is attached to the ends of the tubular body. In other words, the flexible membrane is attached to the tubular body in the region where the blood pump is anastomosed to the resected blood vessel.

The port may be disposed approximately centrally along the length of the tubular body. However, advantageously, the port is disposed off-centre along the length of the tubular body such that the port is nearer the first end than the second end, thereby enabling the blood pump to preferentially pump blood along the blood passageway from the first end towards the second end. In other words, once the blood pump has been implanted in a patient, the port is located proximally to preferentially pump blood in a proximal-to-distal direction.

Advantageously, the blood pump further comprises one or more baffles in the fluid chamber to channel fluid in a direction from the first end towards the second end as it enters the fluid chamber, thereby enabling the blood pump to preferentially pump blood along the blood passageway from the first end towards the second end. In one embodiment, the baffles comprise a spiral configuration.

Advantageously, the flexible membrane has elastic properties.

Advantageously, the blood pump further comprises a check valve arranged to allow fluid to flow through the blood passageway in one direction only.

The tubular body may be rigid or may be flexible. Advantageously, the tubular body comprises a flexible material. More advantageously, the tubular body comprises one or more non-stretch elements for preventing the tubular body from distending significantly when fluid flows into the fluid chamber. For example, the non-stretch elements may be non-stretch filaments having a spiral, axial or annular configuration with respect to the tubular body.

Advantageously, the tubular body has a smooth outer profile.

According to a second aspect of the present invention, there is provided a blood pump system comprising: a blood pump in accordance with the first aspect of the present invention, a fluid conduit coupled to the port of the blood pump, and a drive unit coupled to the fluid conduit and operable to drive fluid alternately into and out of the fluid chamber via the fluid conduit.

In one embodiment, the blood pump system further comprises a pressure sensor operable to measure pressure in the fluid conduit, and the drive unit is responsive to the measured pressure. Alternatively/additionally, the blood pump system further comprises a pressure sensor operable to measure pressure in the fluid chamber, and the drive unit is responsive to the measured pressure.

Optionally, the blood pump system further comprises an electrocardiograph, and the drive unit is responsive to electrocardiographic data.

Advantageously, the drive unit is operable to drive the blood pump in counter-pulsation with the patient's heart.

Advantageously, a porous biocompatible material is attached to an outer surface of a portion of the fluid conduit.

In one embodiment, the drive unit is portable and wearable by a patient.

According to a third aspect of the present invention, there is provided a method for the treatment of heart failure in a patient. The method comprises: resecting a portion of a blood vessel of the patient; anastomosing a pulsatile blood pump of the first aspect into the resected blood vessel; providing a fluid conduit which extends percutaneously out of the patient from the port of the blood pump; and driving fluid along the fluid conduit alternately into and out of the fluid chamber of the blood pump, thereby enabling the blood pump to pump blood along the blood passageway.

In one embodiment, the blood vessel is the ascending aorta.

Advantageously, the method further comprises measuring a pressure within the fluid conduit, and the driving of fluid along the fluid conduit is responsive to the measured pressure. Advantageously, the method further comprises measuring a pressure within the fluid chamber, and the driving of fluid along the fluid conduit is responsive to the measured pressure. Advantageously, the method further comprises measuring electrocardiographic data of the patient, and the driving of fluid along the fluid conduit is responsive to the measured electrocardiographic data. The driving of fluid along the fluid conduit may also be responsive to both pressure and electrocardiographic measurements.

Advantageously, the blood pump is driven in counter-pulsation with the patient's heart.

In one embodiment, the method further comprises surgically repairing the patient's aortic valve before anastomosing the blood pump end-to-end within the resected blood vessel.

In one embodiment, the method further comprises correcting the underlying cardiac defect leading to the patient's heart failure.

According to a fourth aspect of the present invention, there is provided a method for augmenting the perfusion of a patient's limbs and/or organs and/or tissue. The method comprises: resecting a portion of a peripheral blood vessel of the patient; anastomosing a pulsatile blood pump of the first aspect into the resected blood vessel; providing a fluid conduit which extends percutaneously out of the patient from the port of the blood pump; and driving fluid along the fluid conduit alternately into and out of the fluid chamber of the blood pump, thereby enabling the blood pump to pump blood along the blood passageway.

This technique could be used in the popliteal artery, for example, for perfusing limbs or in other arteries for perfusing end organs.

Other preferred features of the present invention are set out in the appended claims.

BRIEF DESCRIPTION OF THE DRAWINGS

Embodiments of the present invention will now be described by way of example with reference to the accompanying drawings in which:

FIG. 2 is a lateral cross-sectional view of a pulsatile blood pump according to one embodiment of the present invention;

FIG. 3 is an axial cross-sectional view of the pulsatile blood pump of FIG. 2;

FIG. 7 shows schematic perspective views of pulsatile blood pumps according to embodiments of the present invention showing three ways of incorporating non-stretch filaments into the tubular bodies of the blood pumps;

FIG. 8 shows two lateral cross-sectional views of pulsatile blood pumps according to embodiments of the present invention, both of which configured are to pump blood in a preferred direction shown by the arrow B;

DETAILED DESCRIPTION OF A PREFERRED EMBODIMENT

Figure 1:
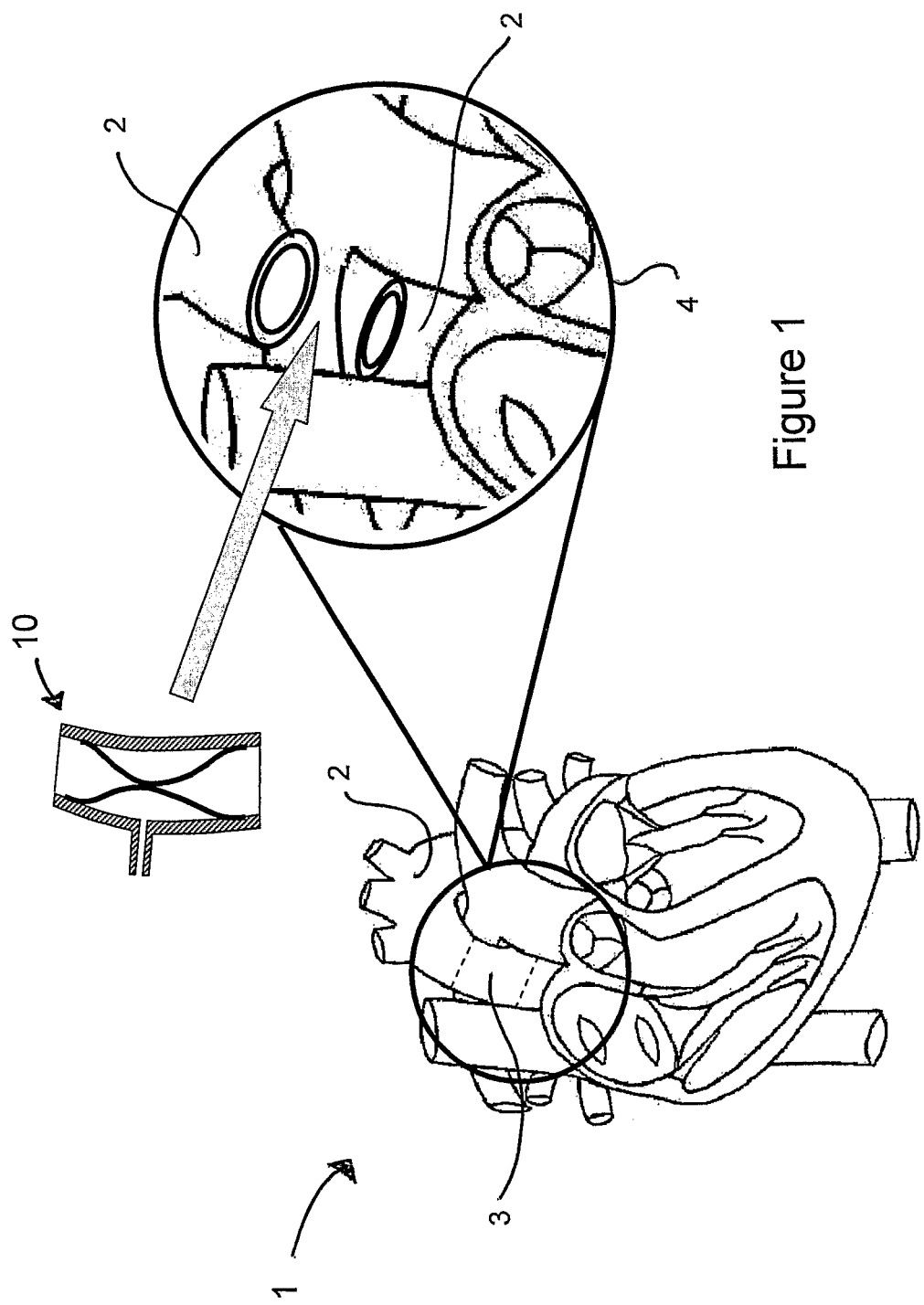
FIG. 1 is a schematic diagram of the heart with an enlarged partial view showing a section of the aorta removed to enable insertion of a pulsatile blood pump according to one embodiment of the present invention.

FIG. 1 shows a schematic representation of a human heart 1. A healthy heart 1 pumps blood to the body via the aorta 2. According to a preferred embodiment of the present invention, a portion 3 of the aorta 2 is resected, as shown in the enlarged view 4 of FIG. 1, and replaced by a pulsatile blood pump 10 placed interpositionally within the aorta 2 just distal of the aortic root and the remainder of the heart 1. The blood pump 10 may then be activated intermittently for short periods as required, or may be activated continuously for periods of limited duration. Therefore, this embodiment of the present invention provides a small pulsatile blood pump 10 having a volume of between 10 and 70 mL which may be permanently incorporated into the aorta 2 as an interpositional graft. In order to place the blood pump 10 in its desired position close to the heart 1, a section 3 of the aorta 2 must be removed. Thus, the blood pump 10 is positioned in the aorta 2 by end-to-end anastomosis (i.e. interpositionally).

A blood pump 10 in accordance with an embodiment of the present invention will now be described in more detail with reference to FIG. 2 which shows such a blood pump 10 in situ in the aorta 2 of a human patient. The resected portion 3 of the aorta 2 is not shown in FIG. 2. The blood pump 10 comprises a substantially tubular body 12 and a flexible membrane 14. The tubular body 12 comprises a port 16 which allows fluid to flow in and out.

The tubular body 12 has a first end 18 and a second end 20. The first end 18 is attached to a first portion 2a of the aorta 2 and the second end 20 is attached to a second portion 2b of the aorta 2 such that blood flows substantially away from the heart 1 in a direction from the first end 18 towards the second end 20 as shown by the arrow B.

The flexible membrane 14 is formed as a tube and is attached concentrically within the tubular body 12 so as to line an inner surface 24 of the tubular body 12. Thus, a fluid chamber 22 is formed between the flexible membrane 14 and the inner surface 24 of the tubular body 12. The fluid chamber 22 is therefore partially bounded by the flexible membrane 14 and partially bounded by the inner surface 24 of the tubular body 12. A blood passageway 26 extends between the first and second ends 18 and 20 of the tubular body 12 and is at least partially bounded by the flexible membrane 14. Thus, the flexible membrane 14 separates the fluid chamber 22 from the blood passageway 26. This is most clearly seen in the axial cross-sectional view of the blood pump 10 of FIG. 3 which is a view looking along the axis of blood flow that shows the blood passageway 26 disposed concentrically within the fluid chamber 22.

The port 16 in the tubular body 12 enables fluid to flow into and out of the fluid chamber 22 of the blood pump 10. Thus, the port 16 is connected to a fluid conduit 28 to carry fluid towards and away from the fluid chamber 22 of the blood pump 10.

Figure 4:
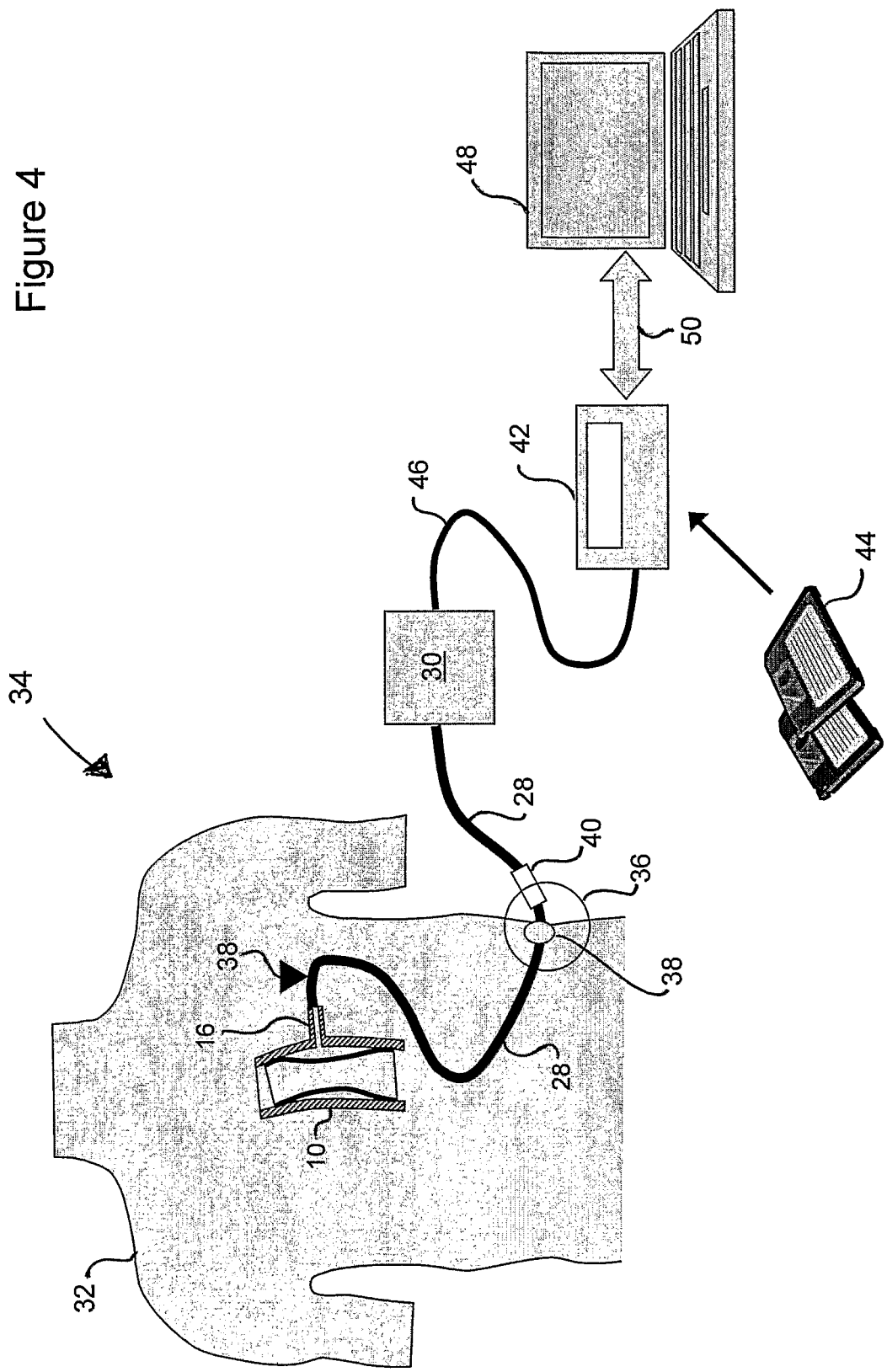
FIG. 4 is a schematic representation of a blood pump system incorporating the pulsatile blood pump of FIG. 2.

A blood pump system 34 incorporating the blood pump 10 of the present invention is shown schematically in FIG. 4. The blood pump 10 (not to scale) is shown implanted within the patient's body 32. The fluid conduit 28, which couples to the port 16 of the blood pump 10, is shown to exit the patient's body 32 percutaneously at the exit site 36. A pressure sensor 38 may be provided to measure the pressure within the fluid conduit 28 close to the blood pump 10. Alternatively or additionally, a pressure sensor (not shown) may be incorporated into the tubular body 12 of the blood pump 10 to measure pressure within the fluid chamber 22.

The fluid conduit 28 is attached to the port 16 of the blood pump 10 in such a way that it may not become detached accidentally. For example, the connection may have a locking mechanism. The connection between the fluid conduit 28 and the port 16 is also detachable such that the fluid conduit 28 may be easily replaced if it becomes infected. Barbed, snap-lock or screw connectors may all be appropriate methods of connection here, along with others. The fluid conduit 28 is flexible and biocompatible. Silicone or PVC are examples of materials appropriate for its construction.

It is desirable to assist tissue incorporation into the exit site 36 so as to prevent infection tracking up the portion of the fluid conduit 28 within the patient's body 32. This may be achieved by wrapping a biocompatible and porous material 38 around the fluid conduit 28 at the exit site 36. Woven or felt polyester or polytetrafluoroethylene (PTFE) may well be best suited to this purpose. As shown in FIG. 4, the material 38 is wound around the fluid conduit 28 right at the exit site 36 so as to become incorporated into the patient's body tissue. The material 38 might extend along a substantial portion of the fluid conduit 28 even up to the pump 10 so as to allow a substantial degree of tissue incorporation and resistance to infection tracking.

A distal end of the fluid conduit 28 is coupled to a drive unit 30 which is an electromechanical device operable to drive fluid alternately into and out of the fluid chamber 22 via the fluid conduit 28 and the port 16. The drive unit 30 may be a conventional console similar to those used in known IABPs when the patient is confined to bed (e.g. when the patient is hospitalised). However, since there is no femoral cannula, the patient is ambulatory and treatment could be delivered in a surgical ward or even in a hostel or at home rather than in an intensive or cardiac care unit. Alternatively, the drive unit 30 may be a small battery powered wearable device so that patients can, be treated completely untethered.

The fluid may be a liquid or a gas, so that the drive unit 30 is operable to provide pulses of hydraulic or pneumatic fluid flow into the fluid conduit 28. In common practice, the pneumatic fluid might be air, carbon dioxide, helium or any readily available non-toxic gas. A hydraulic fluid might be water or any readily available non-toxic liquid.

FIG. 4 additionally shows an optional connector 40 which forms part of the fluid conduit 28 between the exit site 36 and the drive unit 30. In periods where the blood pump 10 is not in use, the drive unit 30 may be disconnected from the blood pump 10 by means of this connector 40. In FIG. 4, the connector 40 is disposed just outside the surface of the skin (i.e. just outside the patient's body 32). Alternatively, the connector 40 may be implanted just below the skin surface of the patient's body 32. In either case, the use of the connector 40 allows the portion of the fluid conduit 28 outside the patient's body 32 to be easily replaced should it become damaged.

Also shown in FIG. 4 is a control unit 42 which is programmable and operable to run software 44 to control the drive unit 30. Thus, there is provided a cable 46 coupled between the drive unit 30 and the control unit 42 to allow data communication therebetween. The control unit 42 may be used to set up controllable parameters of the drive unit 30 and/or to download patient and blood pump data which may be stored on the drive unit 30. Either the drive unit 30 or the control unit 42 might be able to communicate with a remote computer or network 48 so as to remotely configure the system 34 onto monitor its performance and/or patient data. Communication with the remote computer or network 48 is via telecommunication means 50 such as a telephone line, Internet connection, Bluetooth, Wi-Fi or similar.

Figure 5:
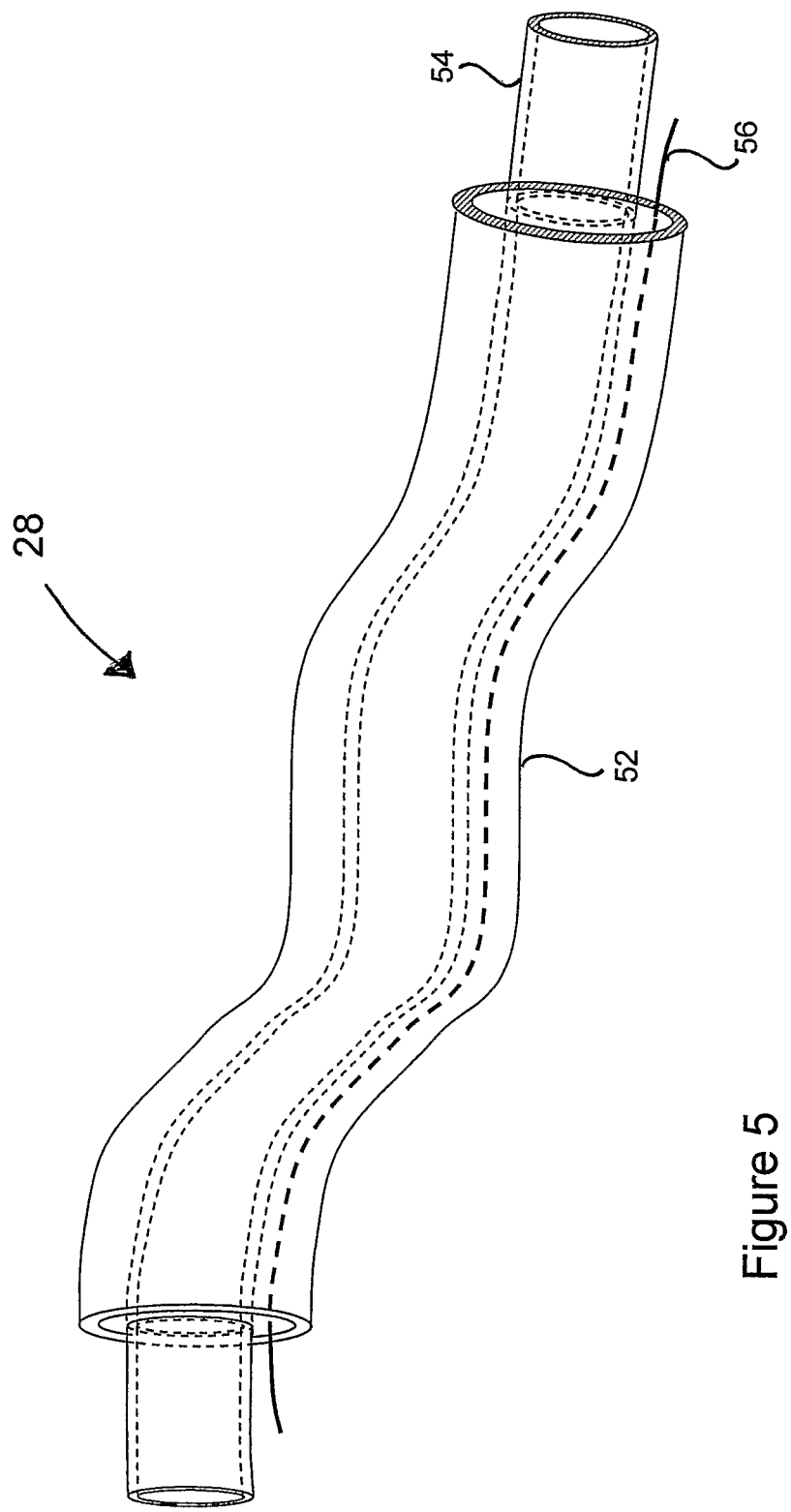
FIG. 5 shows a fluid conduit to convey fluid into and out of a fluid chamber of the pulsatile pump of FIG. 2.

One embodiment of the fluid conduit 28 is shown in more detail in FIG. 5. The fluid conduit 28 comprises an outer layer 52 disposed concentrically around an inner tube 54. The outer layer 52 is an armouring layer which enables the fluid conduit 28 to withstand a degree of mechanical loading (e.g. twisting, flexing, tension and/or crushing) without sustaining any significant damage. The inner tube 54 conveys the hydraulic or pneumatic fluid from the drive unit 30 to the fluid chamber 22 of the blood pump 10. A data cable 56 is disposed between the outer layer 52 and the inner tube 54. The data cable 56 provides data communication between the blood pump 10 and any pressure sensors (e.g. pressure sensor 38), ECG sensors, or implanted devices. In an alternative embodiment, the data cable 56 may be disposed within the inner tube 54. Advantageously, since the fluid conduit 28 is not disposed in the patient's blood stream, it poses a much reduced risk of infection than does an IABP cannula.

In use, the balloon pump 10 is permanently implanted into a patient's blood vessel by end-to-end anastomosis. In a preferred embodiment, the balloon pump 10 is implanted into the aorta 2 as shown in FIGS. 1 and 2. In particular, a section 3 of the lower ascending aorta 2 is resected (see FIG. 1), and the blood pump 10 is grafted in its place via an end-to-end anastomosis as shown in FIG. 2. Grafting may be through sewing the blood pump 10 into place, or may use bioglue or other mechanical attachment. The outer surface 25 of the blood pump 10 and the regions at which the blood pump 10 is anastomosed to the aorta 2 (i.e. the ends 18 and 20) should be relatively smooth so as not to erode neighbouring structures.

The drive unit 30 alternately develops relatively high and low pressures which cause pneumatic or hydraulic fluid to flow along the fluid conduit 28 into and out of the fluid chamber 22 of the blood pump 10. The ingress and egress of pneumatic or hydraulic fluid through port 16 is indicated by double-headed arrow A in FIG. 2. When the drive unit 30 develops a relatively high pressure, fluid is driven hydraulically or pneumatically along the fluid conduit 28, through the port 16, and into the fluid chamber 22. The pressure of the fluid ingress flexes the flexible membrane 14 such that the volume of the inner chamber 22 increases. In particular, the flexible membrane 14 is forced away from the inner surface 24 of the tubular body 12 and the tubular flexible membrane 14 contracts concentrically. Consequently, there is a decrease in the radius and volume of the blood passageway 26 through the centre of the tubular body 12 of the blood pump 10, and this decrease in volume forces blood out of the second end 20 of the tubular body 12 in the direction shown by arrow B. When the drive unit 30 develops a relatively low pressure, fluid is driven hydraulically or pneumatically out of the fluid chamber 22 through the port 16 and into the fluid conduit 28. In this case, the volume of the fluid chamber 22 decreases and there is a corresponding increase in the volume of the blood passageway 26 such that blood is drawn into the first end 18 of the tubular body 12. Thus, the blood passageway 26 remains essentially circular in cross-section during the use of the blood pump 10, but the diameter of the blood passageway 26 increases and decreases with the flexing of the flexible member 14.

Therefore, the fluid chamber 22 is alternately expanded and contracted as the flexible membrane 14 is inflated and deflated by the action of the hydraulic or pneumatic fluid flow from the drive unit 30. In other words, as the flexible membrane 14 is flexed by the flow of fluid into and out of the fluid chamber 22, the cross-sectional area of the blood passageway 26 changes so as to aid in the pumping of blood along the aorta 2. The flexing of the flexible membrane 14 is shown by double-headed arrows C in FIGS. 2 and 3. In this way, the blood pump 10 aids the normal flow of blood through the aorta 2 in the normal flow direction shown by arrow B.

Figure 6:
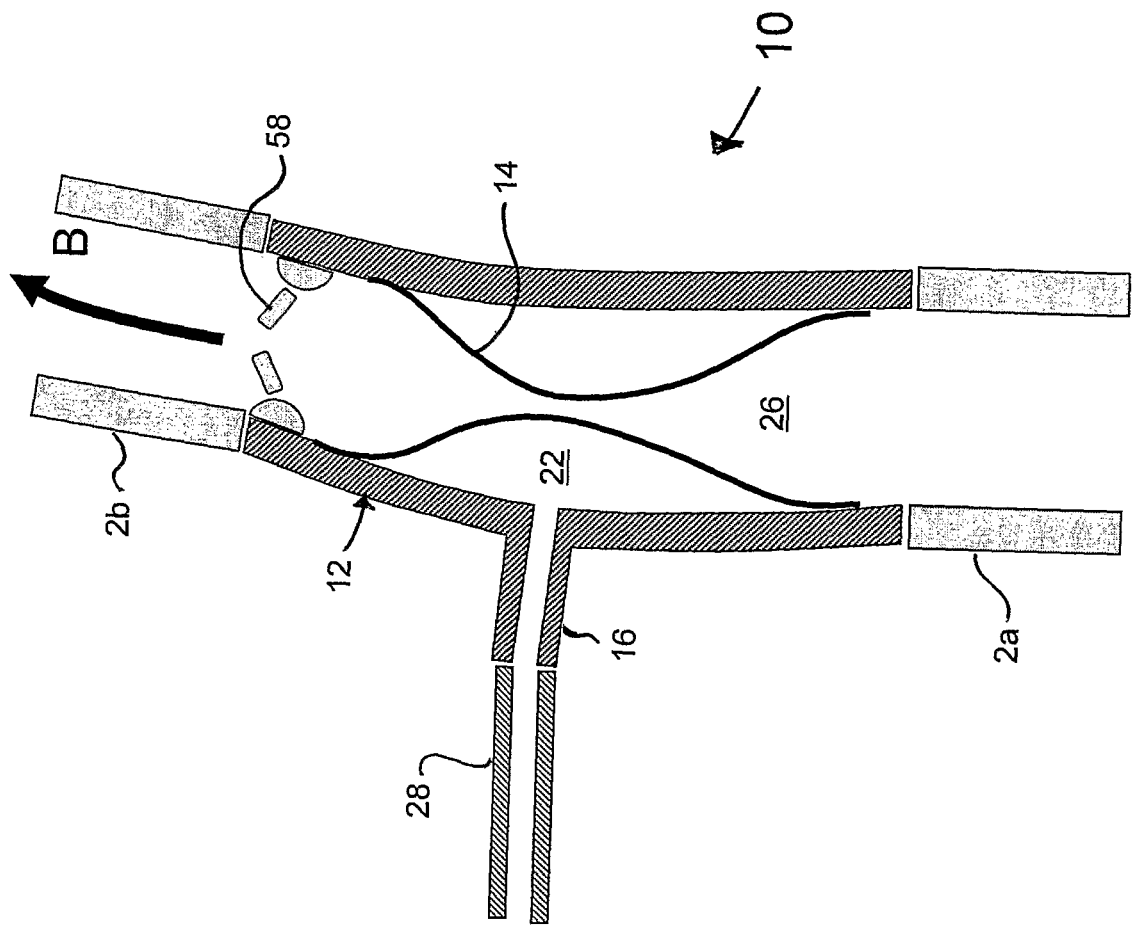
FIG. 6 shows a lateral cross-sectional view of an embodiment of a pulsatile blood pump having a built-in one-way check valve.

Retrograde flow (i.e. flow in the opposite direction to that indicated by arrow B), is prevented by the action of the heart's aortic valve. If the patient's aortic valve is not competent to function, then there are two possibilities. One option is to surgically repair the patient's aortic valve at the time of implantation of the blood pump 10. Alternatively/additionally, the blood pump 10 may itself include a prosthetic heart valve. This option is shown in the embodiment of FIG. 6 which shows the blood pump 10 including a check valve 58 (i.e. a one-way flow valve) which only allows blood to flow through the blood passageway 26 of the tubular body 12 in the direction of normal blood flow, as shown by arrow B. The check valve 58 may be included even if the patient's aortic valve is functional. In this case, the additional check valve 58 may further augment the action of the blood pump 10.

The pressure sensor 38 (and/or other pressure sensors described above) is used to assist with the timing of the fluid flow into and out of the fluid chamber 22 of the blood pump 10. In particular, the pressure measurements from the pressure sensor 38 (and/or other pressure sensors described above) are relayed to the drive unit 30 and/or the control unit 42. In a preferred embodiment, the contraction of the blood pump 10 is controlled such that it occurs in anti-phase with the contractions of the natural heart 1. In other words, when the heart 1 is in diastole, the blood pump 10 is in systole, and vice-versa. Other measurements may also be used to control the timing and/or amount of fluid flow into and out of the fluid chamber 22. For example, an electrocardiograph (not shown) may additionally be provided to monitor electrocardiographic data from the patient's heart. In this case, the drive unit 30 and/or the control unit 42 may be coupled to the electrocardiograph to receive the measured data. The drive unit 30 and the control unit 42 may be separate devices as shown in FIG. 4, or may alternatively be part of a single integral device, which may be portable and wearable by a patient, as described above.

The beneficial effect of the blood pump 10 of the present invention on the heart 1 derives from the aorta 2 being partially "emptied" and more readily distensible with the next cardiac ejection. This reduces the amount of work the heart 1 has to do and allows a degree of recovery and demodelling (reverse re-modelling) of the myocardium. It is envisaged that the blood pump 10 would operate for a support period of around two weeks, after which the blood pump 10 would will be turned off and remain dormant until the next programmed or emergency support period. Experience with related devices suggests no ill effects in the period of dormancy.

The blood pump 10 is implanted operatively. This provides the opportunity for a surgeon to anatomically correct the underlying cardiac defect leading to heart failure (e.g. valve disease, coronary artery disease, cardiomyopathies). This defect correction, when combined with the subsequent intermittent use of the blood pump 10, should significantly improve the patient's prognosis. Furthermore, the operation costs are likely to be significantly lower than the cost of inserting an LVAD, and recovery periods are likely to be much shorter.

Both the tubular body 12 and the flexible membrane 14 are impermeable to the hydraulic or pneumatic fluid used to inflate and deflate the fluid chamber 22.

In a preferred embodiment, the flexible membrane 14 is stretchable (i.e. distendable/elastic/resilient). Alternatively, the flexible membrane 14 may simply be flexible (i.e. bendy but not stretchy). However, a stretchy flexible membrane 14 is preferred so as to reduce the chance of parts of the flexible membrane 14 blocking the blood passageway 26 when the fluid chamber 22 is almost empty of fluid. The flexible membrane 14 may be fabricated from silicone or another biocompatible flexible and distensible material.

The tubular body 12 may be rigid. However, it is preferred that the tubular body 12 has a degree of flexibility to allow it to bend with each heartbeat. Flexibility of the tubular body 12 is also important so that the blood pump 10 does not interfere with or erode neighbouring structures. In one embodiment, the tubular body 12 of the blood pump 10 is fabricated from polyester (e.g. woven polyester fibre) or polytetrafluoroethylene (PTFE). Alternatively, the tubular body 12 may be fabricated from silicone, but any biocompatible material including metals such as titanium might be appropriate.

It will be appreciated that the degree of flexibility of the tubular body 12 should be less than that of the flexible membrane 14. This relative lack of flexibility of the tubular body 12 ensures that it is the flexible membrane 14 which deforms due to the flow of fluid into and out of the fluid chamber 22, rather than it being the tubular body 12 which deforms in response to the fluid flow. In use, the volume of the tubular body 12 remains substantially constant during the flow of fluid into and out of the fluid chamber 22. Thus, the deformation of the flexible membrane 14 allows the volume (and the cross-sectional area) of the blood passageway 26 to vary in use so that the blood pump 10 pumps blood.

In order to provide the tubular body 12 with controlled flexibility, the tubular body 12 may comprise a flexible material and may also incorporate relatively non-stretchable elements such as carbon, carbon fibre or Kevlar fibres, filaments, windings, metallic springs, or similar to constrain the tubular body 12 axially and/or radially. These non-stretchable elements may be applied in a variety of orientations including alternate spirals 60, as shown in FIG. 7a, axial filaments 62 as shown in FIG. 7b, hoop-wise windings 64 as shown in FIG. 7c, or any combination thereof. Other configurations of non-stretchable elements are also envisaged within the scope of the invention.

In preferred embodiments, the blood pump 10 preferentially pumps blood along the blood passageway 26 in a particular axial direction. The blood pump should then be implanted in the patient's blood vessel in the correct orientation such that the preferential pumping direction corresponds to the normal direction of blood flow along the blood vessel. This normal direction of blood flow is from the first end 18 towards the second end 20 of the tubular body 12 as shown by arrow B in the Figures. FIGS. 8*a* and 8*b* show lateral cross sections of pumps having a preferential pumping direction along arrow B.

In FIGS. 8*a* and 8*b*, the port 16 is not centrally disposed along the length of the tubular body 12 in an axial direction. In particular, the port 16 is located nearer the first end 18 than the second end 20. Thus, as hydraulic or pneumatic fluid flows into the fluid chamber 22, it fills the fluid chamber in a direction from the first end 18 towards the second end 20. This in turn imparts momentum to the blood within the blood passageway 26 in the preferred direction from the first end 18 towards the second end 20 as indicated by arrow B.

In FIG. 8*b*, baffles 66 are additionally provided within the fluid chamber 22. The baffles 66 are flexible and collapsible and are formed in a spiral configuration so as to further constrain the hydraulic or pneumatic fluid to flow in the preferred direction from the first end 18 towards the second end 20. In particular, the baffles 66 serve to constrain the flow of fluid within the fluid chamber 22 such that fluid does not reach the second (far) end of the fluid chamber until the first (near) end of the fluid chamber has been filled with fluid. This again imparts momentum on the blood within the blood passageway 26 in the preferred direction indicated by arrow B.

Figure 9:
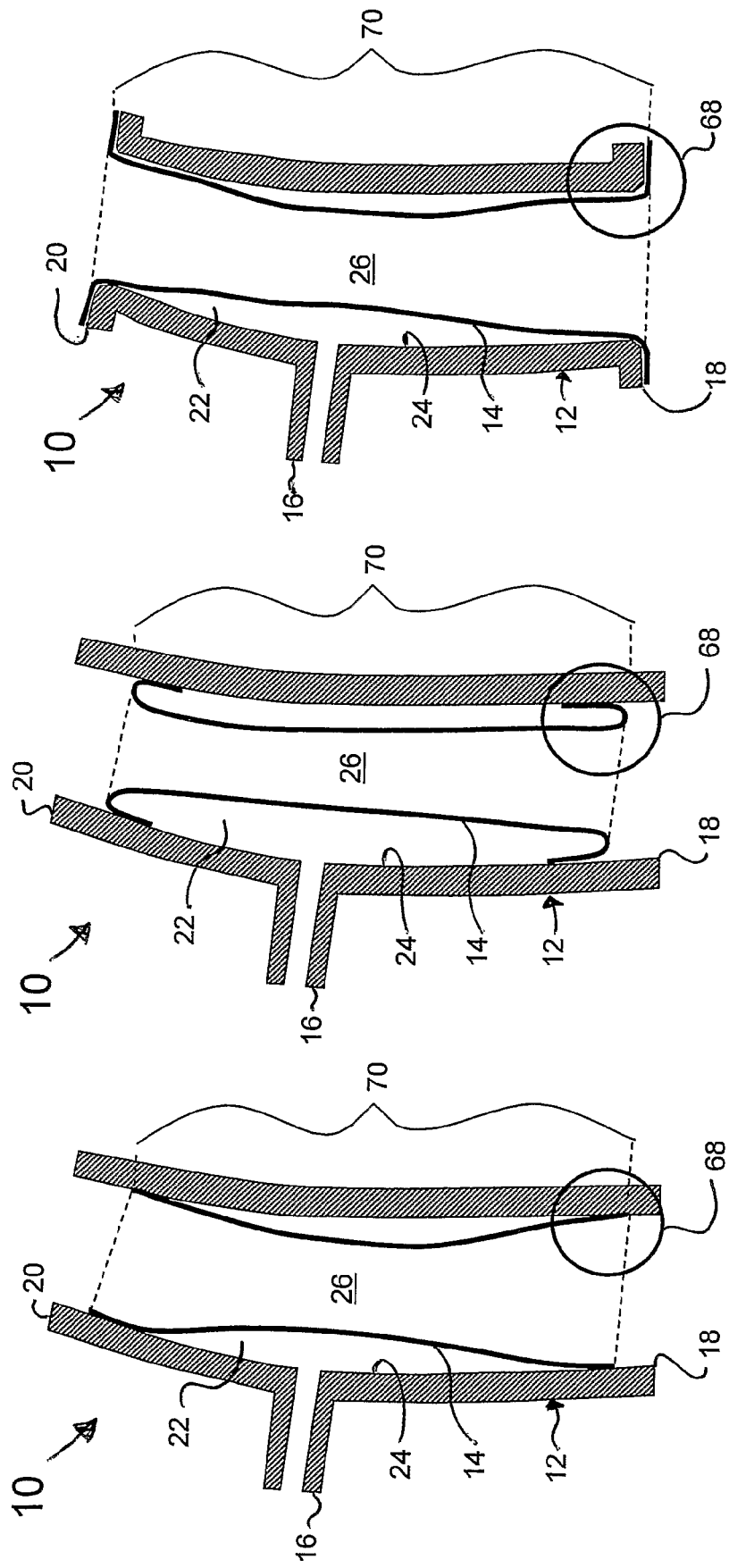
FIG. 9 shows three lateral cross-sectional views of pulsatile blood pumps according to embodiments of the present invention showing different ways of attaching a flexible membrane of the pump to the tubular body of the pump.

FIG. 9 depicts three different ways of attaching the flexible membrane 14 to the tubular body 12. In each case, the flexible membrane is attached at/near the first and second ends 18 and 20 of the tubular body so as to formed a sealed watertight/airtight fluid chamber 22 within the tubular body 12.

The configuration shown in FIG. 9*a* is the same as that shown in FIGS. 2, 6 and 8. In particular, the flexible membrane 14 is attached to the tubular body 12 such that the flexible membrane 14 runs essentially parallel to the tubular body 12 in the attachment regions 68 of the flexible membrane 14 to the tubular body 12. Thus, the tubular flexible membrane 14 essentially sits flush to the inner surface 24 of the tubular body 12 when the fluid chamber 22 is empty. In FIG. 9*a*, the active region 70 of the blood pump 10 does not extend along the full axial length of the tubular body 12 since the attachment regions 68 of the flexible membrane 14 to the tubular body 12 are located near, but not at, the ends 18 and 20. In an alternative embodiment, the tubular flexible membrane 14 could be the same length as the tubular body 12 such that the attachment regions 68 would be at the ends 18 and 20 of the tubular body 12 and the active region 70 would extend along the full axial length of the blood pump 10.

In the configuration of FIG. 9*b*, the flexible membrane 14 is folded over in the attachment regions 70 such that the tubular flexible membrane 14 doubles back on itself in the attachment regions 68. Thus, there is a double thickness of the flexible membrane 14 in the attachment regions 68.

A further alternative configuration is shown in FIG. 9*c* in which the flexible membrane 14 extends out of each end 18 and 20 of the tubular body 12. Thus, the attachment regions 68 are incorporated into the anastomosis regions at each end 18 and 20 of the blood pump 10.

An optimum configuration for attachment of the flexible membrane 14 to the tubular body 12 yield less stress on the flexible membrane 14, the attachments regions 68 and the tubular body 12. This reduces the likelihood of thrombus formation and blood-flow disturbance, and thereby increases longevity and biocompatibility of the blood pump 10. Depending on the situation, the optimum configuration may be accomplished with any combination of the attachments shown in FIGS. 9*a*-9*c*, and the attachment methods may be dissimilar at the first and second ends 18 and 20.

Figure 10:
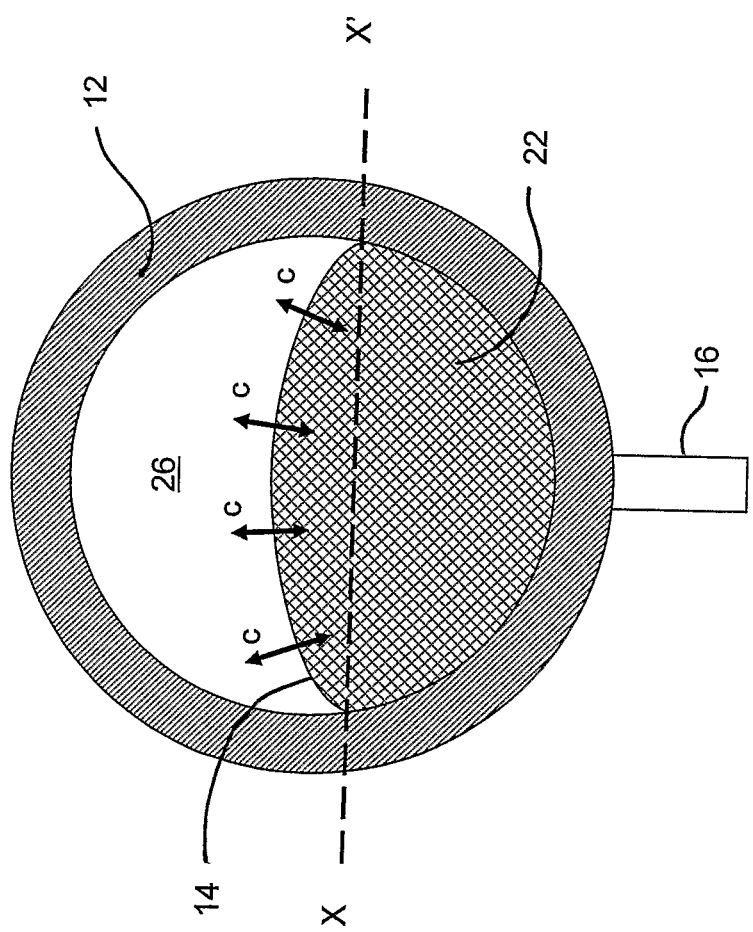
FIG. 10 shows an axial cross-sectional view of an alternative embodiment of a pulsatile blood pump with a different configuration of the flexible membrane within the tubular body.

As shown in FIG. 10, the flexible membrane 14 may be formed as a sheet rather than as a tube. In this embodiment, the flexible membrane 14 is disposed in a chord-like manner across the circular cross-section of the tubular body 12. The appropriate chord is shown by dashed line XX' in FIG. 10. Thus, the flexible membrane 14 divides the tubular body 12 into two axial compartments, one of which is the fluid chamber 22, and the other of which is the blood passageway 26. Of course, the flexible membrane 14 is also attached to the tubular body 12 at or near the ends 18 and 20 such that the fluid chamber 22 is completely enclosed and the pneumatic or hydraulic fluid is separated from the patient's blood by means of the flexible membrane 14. In this embodiment, the fluid chamber 22 expands and contracts eccentrically, rather than concentrically as in the embodiment of FIGS. 2 and 3. Concentric actuation allows the greatest displacement of blood for a given size of blood pump 10. Eccentric actuation may be desirable in some anatomical locations where concentric actuation would obstruct'important features, e.g. at the root of the ascending aorta where concentric actuation may obstruct the coronary arteries.

The present invention therefore provides a new modality or method for treatment of heart failure which has been termed Chronic Intermittent Mechanical Support (CIMS) by the inventors. Benefits of the CIMS approach are summarised below:

1. One main benefit of the CIMS approach will be to improve perfusion to the head, coronary arteries and systemic circulation, and to unload the natural (diseased) heart and allow it to recover through a process known as demodelling or reverse-remodelling. Some hearts will recover almost completely allowing CIMS to be discontinued though the blood pump 10 will remain in place in case of relapse. Other hearts will not recover and medical therapies will continue, but will benefit from CIMS as a therapy similar to, but more aggressive than medical respite.

2. Counter-pulsation is a proven and dependable support method which is incorporated into a large number of commercial IABPs and which is also being developed in EABPs.

3. The use of the percutaneous fluid conduit 28 removes the need for cannulation to support the blood pump 10. This has a number of advantages: it reduces the likelihood of septicaemia posed by IABPs; it ameliorates ischemia distal to the insertion point of the cannula; it removes thromboembolic complications caused by tracking a cannula through the veins; and, unlike IABPs, it allows patients to ambulate.

4. Improved durability: since the blood pump 10 does not require delivery via a cannula tip (e.g. a catheter), the choices of material thickness and composition are much less limited and there is greater scope to develop a device of superior longevity and which will eliminate puncture or tearing by atherosclerotic plaque.

5. Reduction of trauma to the aorta by removing the constant interaction between the balloon of an IABP/EABP and the inner surface of the aorta, which can cause abrasion to the endothelium and lead to plaque formation, aneurism and thrombosis and rupture of the aorta.

6. Elimination of atheromatous emboli: unlike EABPs, the blood pump 10 will not act eccentrically within an atherosclerotic section of aorta, and will remove the mechanisms which lead to the formation atheromatous emboli.

7. Reduction in the amount of surface area of non-biological materials lessens the likelihood of: infection, consumption of coagulation products (e.g. platelets), and bleeding.

8. Interpositioning: The blood pump 10 has distinct advantages over EABPs in that it cannot migrate and will not interfere with neighbouring structures (e.g. causing erosion of the pulmonary artery). Interpositioning a CIMS blood pump 10 within the aorta 2 also gives greater flexibility in the profile design and the use of an eccentric blood pump will enable CIMS to be used where Coronary Artery Bypass Grafting (CABG) is necessary.

9. Cost: the cost of LVAD interventions in bridge to transplantation and destination therapy (Long Term Chronic Support, or LOTS) in terms of Quality-Adjusted Life-Year (QALY) is unacceptably high at an envisaged £40,000/QALY for second generation devices. Given the complexity of second and third generation LVADs, it is unlikely that their cost will reduce to acceptable levels of around £20,000/QALY. Given that the QALY for CIMS is likely to be between those of medical and LVAD therapies and that operating, recovery, and device costs are envisaged to be significantly lower, CIMS offers the potential for long-term cardiac support at acceptable cost (£/QALY).

It is entirely feasible that the blood pump 10 and system 34 of the present invention may be adapted for use in other blood vessels (e.g. a peripheral vein or artery) to increase regional or peripheral perfusion of organs or tissue. One example might be insertion of a blood pump 10 into the femoral or popliteal arteries for the treatment of intermittent claudication.

Although preferred embodiments of the invention have been described, it is to be understood that these are by way of example only and that various modifications may be contemplated.

The invention claimed is:

1. A pulsatile blood pump suitable for implantation into a patient in place of a resected portion of an ascending aorta of the patient, the blood pump comprising:
    a substantially tubular body having first and second ends with a blood passageway extending therebetween for the passage of blood between said first end and said second end;
    a flexible membrane attached to the tubular body to form a fluid chamber between the flexible membrane and an inner surface of the tubular body, the flexible membrane thereby separating the fluid chamber from the blood passageway; and
    a port in the tubular body arranged to allow fluid to flow into and out of the fluid chamber such that the volume of the fluid chamber increases and the volume of the blood passageway decreases when fluid flows into the fluid chamber via the port, and such that the volume of the fluid chamber decreases and the volume of the blood passageway increases when fluid flows out of the fluid chamber via the port, wherein said tubular body is configured so that blood within the blood passageway is not precluded from flowing through both the first and second ends and further wherein the tubular body has no check valves.

2. The blood pump of claim 1, wherein the flexible membrane is formed as a sheet and is attached across a chord of the tubular body such that the fluid chamber and the blood passageway are disposed side by side within the tubular body.

3. The blood pump of claim 1, wherein the flexible membrane is formed as a tube and is attached at or near the first and second ends of the tubular body such that the blood passageway is disposed concentrically within the fluid chamber.

4. The blood pump of claim 1, wherein the flexible membrane is attached to the inner surface of the tubular body.

5. The blood pump of claim 1, wherein the flexible membrane is attached to the first and second ends of the tubular body.

6. The blood pump of claim 1, wherein the flexible membrane has elastic properties.

7. The blood pump of claim 1, wherein the tubular body is formed from a rigid material.

8. The blood pump of claim 1, wherein the tubular body is formed from a flexible material.

9. The blood pump of claim 8, wherein the tubular body comprises one or more non-stretch elements to prevent the tubular body from distending significantly when fluid flows into the fluid chamber.

10. The blood pump of claim 9, wherein the non-stretch elements are non-stretch filaments having a spiral, axial or annular configuration with respect to the tubular body.

11. A blood pump system comprising:
    a blood pump according to claim 1;
    a fluid conduit coupled to the port of the blood pump; and
    a drive unit coupled to the fluid conduit and operable to drive fluid alternately into and out of the fluid chamber via the fluid conduit.

12. The blood pump system of claim 11 further comprising:
    a pressure sensor operably positioned to measure pressure in the fluid conduit, wherein the drive unit is responsive to the measured pressure.

13. The blood pump system of claim 11 further comprising:
    a pressure sensor operably positioned to measure pressure in the fluid chamber, wherein the drive unit is responsive to the measured pressure.

14. The blood pump system of claim 11 further comprising:
    an electrocardiograph, wherein the drive unit is responsive to data from the electrocardiograph.

15. The blood pump system of claim 11, wherein the drive unit is positioned to drive the blood pump in counter-pulsation with the patient's heart.

16. The blood pump system of claim 11, wherein a porous biocompatible material is attached to an outer surface of a portion of the fluid conduit.

17. The blood pump system of claim 11, wherein the drive unit is portable and wearable by a patient.

18. A method for the treatment of heart failure in a patient, the method comprising:
    selecting a patient susceptible of heart failure;
    resecting a portion of an ascending aorta of the selected patient;
    anastomosing the pulsatile blood pump of claim 1 into the resected ascending aorta;
    providing a fluid conduit which extends percutaneously out of the patient from the port of the blood pump; and
    passing fluid within the fluid conduit alternately into and out of the fluid chamber of the blood pump.

19. The method of claim 18 further comprising:
    measuring pressure within the fluid conduit and
    passing fluid within the fluid conduit based on the measured pressure.

20. The method of claim 18 further comprising:
    measuring pressure within the fluid chamber and
    passing fluid within the fluid conduit based on the measured pressure.

21. The method of claim 18 further comprising:
   measuring electrocardiographic data of the patient and passing fluid within the fluid conduit in response to the measured electrocardiographic data.

22. The method of claim 18, wherein the blood pump is driven in counter-pulsation with the selected patient's heart.

23. The method of claim 18 further comprising:
   surgically repairing the patient's aortic valve before said anastomosing the blood pump end-to-end within the resected blood vessel.

24. The method of claim 18 further comprising:
   correcting an underlying cardiac defect leading to the selected patient's heart failure.

\* \* \* \* \*